United States Patent [19]

Van Wijngaarden et al.

[11] Patent Number: 4,889,849
[45] Date of Patent: Dec. 26, 1989

[54] SPASMOLYTICALLY ACTIVE TERTIARY AMINE DERIVATIVES

[75] Inventors: Ineke Van Wijngaarden; Johannes M. A. Zwagemakers; Jan Van Dijk, all of Weesp, Netherlands

[73] Assignee: Duphar International Research B.V., Weesp, Netherlands

[21] Appl. No.: 294,997

[22] Filed: Jan. 9, 1989

Related U.S. Application Data

[63] Continuation of Ser. No. 773,659, Sep. 9, 1985, abandoned.

[30] Foreign Application Priority Data

Sep. 12, 1984 [NL] Netherlands .................. 8402783

[51] Int. Cl.$^4$ .................. A61K 31/535; A61K 31/54; C07D 265/30; C07D 279/06
[52] U.S. Cl. .................. 514/218; 514/183; 514/222.2; 514/237.5; 514/255; 514/278; 514/304; 514/319; 514/327; 514/329; 514/330; 514/423; 540/450; 540/482; 540/575; 544/58.2; 544/162; 544/391; 546/16; 546/132; 546/205; 546/216; 546/223; 546/226; 548/540
[58] Field of Search .................. 540/450, 482, 575; 544/58.2, 162, 391; 546/16, 132, 205, 216, 223, 226; 548/540; 514/183, 218, 222.2, 237.5, 255, 278, 304, 319, 327, 329, 330, 423

[56] References Cited

U.S. PATENT DOCUMENTS

| | | | |
|---|---|---|---|
| 2,654,754 | 10/1953 | Bruce et al. ........................ | 548/540 |
| 3,759,979 | 9/1973 | Beregi et al. .................. | 546/226 X |
| 4,594,343 | 6/1986 | Shanklin et al. ................. | 546/226 X |

OTHER PUBLICATIONS

Clark et al., J. Pharm. Sci., vol. 76, No. 5, (1987), pp. 411–415.
Fournier et al., Eur. J. Med. Chem.—Chim. Ther. 17, (1982), p. 81.

*Primary Examiner*—Richard L. Raymond
*Attorney, Agent, or Firm*—Stevens, Davis, Miller & Mosher

[57] ABSTRACT

The invention relates to new spasmolytically active tertiary amine derivatives and the salts thereof, of the formula (1)

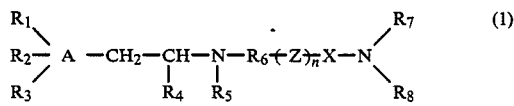

wherein the symbols have the following meanings:

A is phenyl, or a 5- or 6-membered aromatic group containing 1 or 2 of the following hetero atoms: oxygen and/or sulphur and/or nitrogen;

$R_1$ and $R_2$ may be equal or different and are hydrogen or substituents;

$R_3$ is a hydrogen atom or, together with $R_4$, may form a ring consisting of 6 or 7 carbon atoms;

$R_4$ is a hydrogen atom or alkyl group having 1–3 carbon atoms;

$R_5$ is a straight, branched or cyclic alkyl group having 1–4 carbon atoms;

$R_6$ is a straight or branched, saturated or unsaturated alkylene group having a chain length of 2–6 carbon atoms;

Z is the group $NR_{12}$, wherein $R_{12}$ is a hydrogen atom or an alkyl group having 1–3 carbon atoms, or Z is an oxygen atom;

n has the value 0 or 1;

X is a carbonyl group, thiocarbonyl group or $SO_2$ group;

$R_7$ and $R_8$, together with the nitrogen atom to which they are bound, constitute a fully or partly saturated heterocyclic ring consisting of 5–8 ring atoms and which may comprise in addition an O, N or S-atom as the second hetero atom, and may be substituted.

3 Claims, No Drawings

SPASMOLYTICALLY ACTIVE TERTIARY AMINE DERIVATIVES

This application is a continuation of application Ser. No. 773,659, filed Sept. 9, 1985, now abandoned.

The invention relates to spasmolytically active tertiary amine derivatives and the salts thereof, to a method of preparing the said compounds, and to pharmaceutical compositions comprising at least one of the said new compounds or a salt thereof as the active substance.

It is the object of the present invention to find compounds which have a specific spasmolytic effect on the smooth musculature of the tractus gastro-intestinalis, the tractus urogenitalis and the bronchial system without peripheral and preferably also without central muscarinolytic side effects which are characteristic of neurotropic spasmolytics, for example, atropine. The desired effect should occur after oral administration and should be prolonged.

It was surprisingly found that the compounds represented by formula (1) below and the acid addition salts thereof satisfy the above mentioned objects.

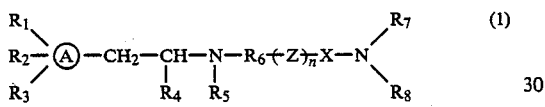

In this formula (1) the symbols have the following meanings:

Ⓐ is phenyl, or a 5- or 6-membered aromatic group containing 1 or 2 of the following hetero atoms: oxygen and/or sulphur and/or nitrogen;

$R_1$ and $R_2$ may be equal or different and are hydrogen, alkyl having 1-3 carbon atoms, hydroxyalkyl or mercaptoalkyl having 1-3 carbon atoms wich may be etherified or esterified, alkoxy having 1-3 carbon atoms, the group $S(O)_m$—$R_9$, wherein $R_9$ is an alkyl group having 1-3 carbon atoms, and m has the value 0, 1 or 2, a group - $NR_{10}R_{11}$, wherein $R_{10}$ and $R_{11}$ represent alkyl having 1-3 carbon atoms, or together may form a saturated, 5 or 6 membered ring which may contain a sulphur, oxygen or nitrogen atom as second hetero atom, $R_1$ and $R_2$ represent an optionally derivated hydroxy group, mercapto group or amino group, or a halogen atom, or $R_1$ and $R_2$ together may form a 5- or 6-membered ring optionally containing 1 or 2 oxygen, and/or nitrogen and/or sulphur atoms, which ring is condensed with Ⓐ, is fully or partly unsaturated and may be substituted by one or more alkyl groups having 1-3 carbon atoms, optionally etherified or esterified hydroxyalkyl having 1-3 carbon atoms or an oxygen atom;

$R_3$ is a hydrogen atom or, together with $R_4$, may form a ring consisting of 6 or 7 carbon atoms;

$R_4$ is a hydrogen atom or alkyl group having 1-3 carbon atoms;

$R_5$ is a straight, branched or cyclic alkyl group having 1-4 carbon atoms;

$R_6$ is a straight or branched, saturated or unsaturated alkylene group having a chain length of 2-6 carbon atoms;

Z is the group $NR_{12}$, wherein $R_{12}$ is a hydrogen atom or an alkyl group having 1-3 carbon atoms, or Z is an oxygen atom;

n has the value 0 or 1;

X is a carbonyl group, thiocarbonyl group or $SO_2$ group;

$R_7$ and $R_8$, together with the nitrogen atom to which they are bound, constitute a fully or partly saturated heterocyclic ring consisting of 5-8 ring atoms and which may comprise in addition an O, N or S-atom as the second hetero atom, and may be substituted by 1 or 2 alkyl groups having 1-3 carbon atoms, an alkylene bridge of 2 or 3 carbon atoms across the ring, or an oxygen atom which, in case of a keto function may optionally have the form of a ketal or oxim, or the ring formed by $R_7$ and $R_8$ may be substituted directly or via an alkylene chain of 1-3 carbon atoms, with 1 or 2 of the following substituents: phenyl or phenyl substituted with halogen, alkyl or alkoxy having 1-3 carbon atoms, hydroxy, amino, mono- or dialkylamino having 1-3 carbon atoms in the alkyl group(s), alkanoyl or thioalkanoyl having 1-3 carbon atoms, hydroxy alkanoyl having 1-3 carbon atoms, benzoyl, optionally esterified or etherified hydroxy or mercapto, optionally mono- or dialkyl and/or -acyl substituted amino, carbalkoxy having 1-3 carbon atoms in the alkoxy group, a carbamoyl, thiocarbamoyl, sulfamoyl or carbamoyloxy group of which the nitrogen atom may be substituted by 1 or 2 alkoxy groups having 1-3 carbon atoms and/or alkyl groups having 1-5 carbon atoms, which, optionally via a nitrogen, oxygen or sulphur atom, may form a substituted or non-substituted saturated heterocyclic group consisting of 5 or 6 ring atoms.

When the group $R_4$ in the above formula (1) has a meaning other than hydrogen, then the carbon atom to which $R_4$ is bound, is a chiral centre. Since the desired spasmolytic effect can be found entirely or substantially entirely in the enantiomer having the S configuration, the invention, in so far as a chiral centre is concerned, relates to the enantiomers of the compound of formula (1) which have the S configuration and to the racemic mixture of the said compounds. The invention also relates to prodrugs of the above-mentioned compounds, i.e. derivatives of the compounds of formula (1) which are inactive as such and which after administration are converted in the body into active compounds of formula (1).

The compounds of the general formula (1) are strong, specifically active spasmolytics. Surprisingly, the spasmolytic effect in vivo is significantly stronger than could be expected on the basis of the in vitro effects on muscarine receptors, while no musculotropic activity could be demontrated. The compounds show a specific neurotropic activity with respect to the smooth musculature of the gastrointestinal system, while other typical muscarinolytic effects on inter alia the parotis, oxyntic cells of the stomach, secretory cells of the gastrointestinal system, the detrusor muscle of the bladder and ciliary muscles of the eye, are absent entirely or substantially entirely (cf. atropine);

Moreover, the compounds of the general formula (1), notably the compounds in which Ⓐ phenyl, $R_1$ is p-$OCH_3$, $R_2$ and $R_3$ are hydrogen, $R_4$ is methyl (whereas the carbon atom to which $R_4$ is bound has the S configuration); $R_5$ is ethyl, $R_6$-$(Z)_n$ is the group —$(CH_2)_3$— and X is the carbonyl group, and the group

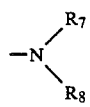

has the following meaning:

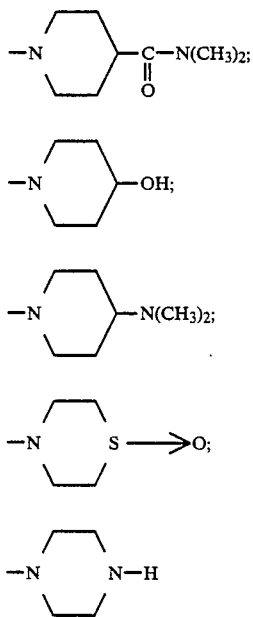

have, in comparison with the strong spasmolytic activity, a surprisingly small centrally acting muscarinolytic activity, as a result of which they are also superior to the specific muscarinolytics known from Netherlands Patent Application 74.04733, and notably secoverine. The specific spasmolytic effect occurs both after parenteral and oral administration and is prolonged.

The substances are ell tolerated. The oral $LD_{50}$ values are above 320 mg per kg in the mouse.

On the basis of the above pharmacological profile, compounds according to the invention are extremely suitable for the treatment of those diseases where spasms or hypermotility of the smooth musculature of the gastrointestinal system, the urogenic system or the bronchial system play a role.

The choice of the dosage depends on the nature and the severity of the disease. On the basis of the animal experiments where the oral spasmolytic dose is between 0.1 and 5.0 mg per kg, the oral human-therapeutic dosages are estimated at 3 to 30 mg per day. With this dose there is little danger for peripheral and/or central side-effects, such as dry mouth, reduced stomach acid secretion, urine retention, accomodation disturbances, photophobia, obstipation, tachycardia or central side effects such as the belladonna syndrome (cf. atropine), while this dose may be increased, if so desired. In the table below, the spasmolytic activity, the ratio of the peripheral side effect to the spasmolytic activity, and the ratio of the central side effect to the spasmolytic activity of the known substances atropine and secoverine are compared with five new compounds of the formula

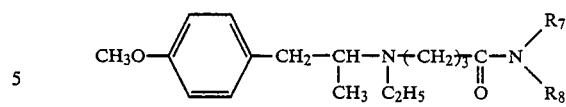

wherein the group $NR_7R_8$ has the meaning mentioned in the table.

TABLE

| Compound (—$NR_7R_8$) | Spasm. activ. | Periph. side effect/ spasm. activity | Centr. side effect/spasm. act. |
|---|---|---|---|
| Atropine | 1 | 1 | 1 |
| Secoverine | 0.6 | 50 | 2 |
| —N⟨piperidine⟩—C(=O)—N(CH₃)₂ | 1 | 30 | 30 |
| —N⟨piperidine⟩—OH | 0.7 | 15 | 8 |
| —N⟨piperidine⟩—N(CH₃)₂ | 0.7 | 30 | 30 |
| —N⟨thiomorpholine S→O⟩ | 0.7 | 70 | 20 |
| —N⟨piperazine⟩N—H | 0.3 | 7 | 10 |

The compounds, in addition to atropine and secoverine, were tested in a number of relevant test models for:

1. Spasmolytic activity in vitro.

1.1 Antimuscarinic activity

Muscarinolytic activity was examined by studying the displacement of (3H)-QNB of muscarinic receptors in a 50.000 g membrane fraction of rat brains (Snyder and Yamamura, Proc. Natl. Acad. Sci., 71, 1725 (1974). The results were expressed in Ki-values.

Antagonism of the contractions of rat jejunum induced by increasing concentrations of furthretonium was used as the second test method (v. Rossum, Arch. Int. Phamacodyn 143, 299 (1963). The results were expressed in $pA_2$ values.

1.2 Calcium antagonism

Calcium antagonistic activity was investigated in the isolated taenia coecum of the guinea pig. The results were expressed in $pA_2$ values.

1.3 Spasmolytic activity versus $BaCl_2$

The antagonism of contractions induced by $BaCl_2$ was determined in the isolated guinea pig ilea. The results were expressed in $pA_2$ values.

2. Spasmolytic activity in vivo.

Effect on the ileum of the guinea pig.

The spasmolytic effect of the compounds was tested on the ilea of urethane-narcotised, empty-stomach guinea pigs of approximately 500 g (Zwagemakers, Arzn. Forsch. 30, 1517 (1980). Contractions of the intestine were induced every 7 minutes with intravenously administered carbachol in a dose of 5 μg per kg of body weight. After constant response had been reached, the test compounds were administered 3 minutes before the next dose of carbachol was given and the protecting effect was studied for 52 minutes. The contractions after administration of the test compounds were expressed as a percentage of the average of two control values. The average percentage of inhibition was calculated throughout the 52 minutes from the region under the curve. The maximum percentage of inhibition and the duration of the spasmolytic effect were also determined. The spasmolytic effect was considered to be finished when two successive contractions were 20% or less of the control value.

3. Muscarinolytic "side effects".

The compounds to be tested and oxotremorine were administered intraperitoneally to femal DAP-mice at the same instant or, in case of analgesia, also 30 minutes previously. The analgesia was determined according to the Chen method 15 minutes after administration of oxotremorine (J. Pharm. Exp. Ther. 124, 73 (1958). Twenty minutes after administration the occurrence of tremors was scored. Simultaneously the presence or absence of saliva secretion or tear secretion was determined. The results obtained were expressed as ED50-values.

Inhibition of the tremors and/or analgesia caused by oxotremorine is a measure of the central muscarinolytic activity, while the inhibition of saliva secretion or tear secretion reflects the peripheral muscarinolytic activity.

The new compounds according to the invention and the salts thereof can be prepared in a manner known for the synthesis of analogous compounds.

Therefore, the invention also relates to a method of preparing new tertiary amines of formula (1) wherein the symbols have the above-mentioned meanings, and the acid addition salts thereof.

Dependent on the meanings of the symbols, the compounds of formula (1) can be obtained by means of one or more of the following methods, for example, by converting a compound of the formula:

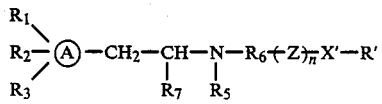 (2)

wherein $R_1-R_6$, Ⓐ, Z and n have the above meanings, X' is the carbonyl group or $SO_2$ group, and R' is an alkoxy group, a hydroxyl group or a halogen atom, with an amine of the general formula:

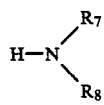 (3)

wherein $R_7$ and $R_8$ have the above meanings. When R' is an alkoxy group, the reaction is preferably carried out in an inert solvent, for example, toluene or dimethyl sulphoxide or without a solvent, with a base as the catalyst, for example sodium hydride or sodium methanolate, at a temperature of 0° to 100° C., preferably at room temperature, for 1-48 hours. When $R_1$ is a hydroxyl group, the reaction is preferably carried out in an inert solvent, for example, $CH_2Cl_2$ or toluene, in the presence of a reagent activating the acid group, for example, ethyl chloroformate or isobutyl chloroformate, 2-chloro-N-methyl pyridinium iodide, diphenyl phosphinyl chloride and the like, whether or not with a base, for example triethyl amine, as a catalyst at a temperature of −40° C. to 100° C. for 1-48 hours. When R' is a halogen atom, preferably chlorine, the reaction is preferably carried out in an inert solvent, for example, acetonitrile, toluene, dichloromethane or 1,2-dichloroethane or in a combination of solvents which, in addition to one of the above inert solvents, contains water; an organic or inorganic base may be added to the reaction mixture, for example, triethyl amine or KOH, or an excess of the amine (3) may be used; the reaction is carried out at −40° C. to 100° C. (preferably at room temperature) for 1 to 48 hours.

The compounds of formula (2) used as starting compounds wherein $R_1-R_6$, Ⓐ, X' have the above meanings and n has the value zero may be obtained, for example, by converting a ketone of the formula

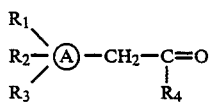 (4)

in the presence of a reducing agent with an amine of the formula

 (5)

into a compound of the formula

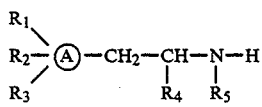 (6)

succeeded by reaction with a compound of the formula:

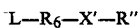 (7)

In these formulae, $R_1-R_6$ and Ⓐ have the above meanings and L is a so-called "leaving group", for example a chlorine atom, a bromine atom or a iodine atom, or a p-toluene suphonyl group, and R" is an alkoxy group.

The reaction of compound (4) with the amine (5) in the presence of a reducing agent is carried out in a manner known per se (Org. React. 4, 174, 1948 and J.A.C.S. 93, 2897, 1971). The reaction of the amine (6) with compound (7) is carried out in a manner known for analogous compounds (Patai "The chemistry of the amino group", pp. 45–55. Interscience publishers, New York, 1968).

The starting substances thus obtained of formula (2), wherein R' (i.e. R" in formula (7)) is an alkoxy group, can be converted into the corresponding compounds (2) wherein R' is a hydroxyl group, by a treatment with an inorganic acid, preferably HCl, or an inorganic base, preferably KOH. These may then be further converted into the corresponding compounds (2) wherein R' is a halogen atom, by means of reagents known for this conversion, for example, thionyl chloride.

Partly, the ketones of formula (4) are known compounds and, in so far as they are new compounds, they can be obtained in a manner known for the preparation of analogous ketones.

The starting compounds (2) wherein $R_1$-$R_6$ 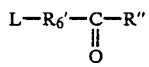 X' and Z have the above meanings, R' is a chlorine atom, and has the value 1, can be obtained, for example, by converting an amine of the formula (6) with a compound of the formula:

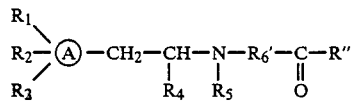   (8)

in which formulae $R_1$-$R_5$, Ⓐ, L and R'' have the above meanings and $R_6'$ together with the keto group after reduction results in the group $R_6$ with the above meaning. In this manner, esters of the formula

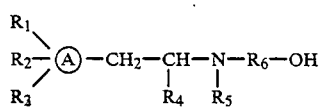   (9)

are obtained. For the preparation of starting substances (2) in which Z is an oxygen atom, the esters (9) are reduced in a manner known per se to the corresponding alcohols of the formula:

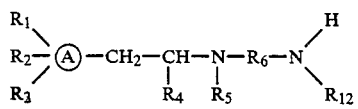   (10)

Starting substances in which Z is the group $NR_{12}$ are obtained in a manner known for analogous compounds by converting the esters (9) into the corresponding amide which is then reduced to an amine of the formula $$\begin{array}{c} R_1 \\ R_2-\text{Ⓐ}-CH_2-CH-N-R_6-N \\ R_3 \qquad\quad R_4 \quad R_5 \qquad\quad R_{12} \end{array} \quad \begin{array}{c} H \end{array} \quad (11)$$

wherein $R_{12}$ has the meaning given hereinbefore.

Reaction of the compounds (10) or (11) with phosgene, or sulphur dioxide and chlorine gas (Ann. Chem. 624, 25, 1959) respectively, results in the desired starting compounds (2), wherein $R_1$-$R_6$, Ⓐ X' have the above meanings, n has the value 1 and Z is an oxygen atom or the group $NR_{12}$, and R' is a chlorine atom.

The compounds of the general fomula (1) wherein X has the meaning C=S can be obtained, for example, by reaction of the corresponding compounds wherein X is the carbonyl group with $P_2S_5$ or with 2,4-bis (4-methoxyphenyl)-1,3,2,4-dithiadiphosphetane 2,4-disulphide in a manner known per se (Synthesis 149, 1973, J. Am. Chem. Soc. 104, 3104, 1982).

Enantiomers of compounds of formula (1) which have a chiral centre can be obtained, for example, by separation of the intermediary amines of the formula (6) according to, or analogous to, a method described in Receuil des Travaux Chimiques des Pays-Bas 85 (6), 607-615, 1966, succeeded by further synthesis in a manner analogous to the synthesis of racemates. The separations can also be carried out with known methods on the final product or on other intermediates.

As examples of pharmaceutically acceptable acids with which the compounds of formula (1) according to the invention form salts may be mentioned' hydrochloric acid, sulphuric acid, phosphoric acid, methanesulphonic acid, p-toluene sulphonic acid, benzoic acid, acetic acid, propionic acid, tartaric acid, succinic acid, citric acid, fumaric acid, maleic acid, etc.

The compounds of formula (1) and the salts thereof can be brought into a form suitable for administration by means of known methods, for example, capsules, tablets, coated tablets, pills, suppositories and plasters for transdermal application.

The invention will now be described in greater detail with reference to the ensuing specific examples. If not stated otherwise, the compounds were obtained as a high-boiling-point oil the boiling-point of which could not be determined as a result of decomposition. The compounds were characterized by means of $^1H$ or $^{13}C$ N.M.R.

EXAMPLE I (S)-1-[4-[ethyl[2-(4-methoxyphenyl)-1-methylethyl]amino]-1-oxobutyl]-N,N-dimethyl-4-piperidine carboxamide.

3.20 g (73 mmol) of NaH dispersion (content 55%) were added under nitrogen to a mixture of 20 ml of dry dimethyl sulphoxide and 10 ml of dry toluene and stirred at room temperature for 30 minutes. While stirring, at 20°-25° C., 6.47 g (33.3 mmol) of N,N-dimethyl-4-piperidine carboxamide hydrochloride were added in small portions and stirred at room temperature for 30 minutes.

A solution of 9.21 g (30 mmol) of (S)-ethyl-4-[ethyl[2-(4-methoxyphenyl)-1-methylethyl]amino]butyrate in 20 ml of dry dimethyl suphoxide and 10 ml of dry toluene was then added dropwise at 20°-25° C. and then stirred at room temperature for 24 hours.

200 ml of water were added to the reaction mixture, the temperature being kept below 30° C. The water layer was acidified with 2N hydrochloric acid until pH 5 and sodium bicarbonate was then added until pH 7 to 8. The whole was then extracted three times with diethyl ether. The water layer was made basic with 2 N NaOH and extracted three times with methylene chloride. The collected organic layers were washed once with little water, dried on sodium sulphate and evaporated under reduced pressure.

The resulting crude base (8.75 g) was purified chromatographically over 100 g of basic aluminum oxide (Baker, Brockmann Activity. Grade I) using a mixture of diethyl ether and methanol (ratio 95:5) as an eluent. The collected fractions were evaporated under reduced pressure. They contained 7.2 g (17.2 mmol) of product. The resulting substance was dissolved in 30 ml of diethyl ether; 15 ml of hexane were added to this solution at reflux temperature. The solution was cooled to 0° C. while stirring, the product crystallizing out.

This resulted in 4.7 g (11.3 mmol) of (S)-1-[4-[ethyl[2-(4-methoxyphenyl)-1-methylethyl]amino]-1-oxobutyl]-N,N-dimethyl-4-piperidine carboxamide (melting-point 68-69° C).

In an analogous manner were prepared'
 1. 1-[4-[ethyl[2-(4-methoxyphenyl)-1-methylethyl]amino]-1-oxobutyl]-2-methyl piperidine 2. 1-[4-[ethyl[2-(4-methoxyphenyl)-1-methylethyl]amino]-1-oxobutyl]-8-1,4-dioxa-8-azaspiro[4,5]decane
3. (S)-1-[4-[ethyl[2-(4-methoxyphenyl)-1-methylethyl]amino]-1-oxobutyl]piperazine
4. 1-[4-[ethyl[2-(4-methoxyphenyl)-1-methylethyl]amino]-1-oxobutyl]piperazine (racemate of 3.)
5. 1-[4-[ethyl[2-(4-methoxyphenyl)-1-methylethyl]amino]-1-oxobutyl]-3-methyl piperazine
6. 1-[4-[ethyl[2-(4-methoxyphenyl)-1-methylethyl]amino]-1-oxobutyl]-4-methyl piperazine
7. 1-[4-[ethyl[2-(4-methoxyphenyl)-1-methylethyl]amino]-1-oxobutyl]-3,5-dimethyl piperazine
8. 1-[4-[ethyl[2-(4-methoxyphenyl)-1-methylethyl]amino]-1-oxobutyl]perhydro-1,4-diazepine
9. 1-[4-[ethyl[2-(4-methoxyphenyl)-1-methylethyl]amino]-1-oxobutyl]morpholine
10. 1-[4-[ethyl[2-methoxy-5,6,7,8-tetrahydro-6-naphthyl]amino]-1-oxobutyl]N,N-dimethyl-4-piperidine carboxamide
11. 1-[4-[ethyl[2-(4-chlorophenyl)-1-methylethyl]amino]-1-oxobutyl]piperazine
12. 1-[4-[ethyl[2-(4-fluorophenyl)-1-methylethyl]amino]-1-oxobutyl]piperazine
13. 1-[4-[ethyl[2-(4-methylthiophenyl)-1-methylethyl]amino]-1-oxobutyl]piperazine
14. 1-[4-[ethyl[2-(3-methyl-4-methoxyphenyl)-1-methylethyl]amino]-1-oxobutyl)-N,N-dimethyl-4-piperidine carboxamide
15. 1-[4-[ethyl[2-(2-methyl-4-methoxyphenyl)-1-methylethyl]amino]-1-oxobutyl]-N,N-dimethyl-4-piperidine carboxamide
16. 1-[4-[ethyl[2-(4-methoxyphenyl)-1-methylethyl]amino]-1-oxobutyl]-4-benzylpiperidine
17. 1-[4-[ethyl[2-(2-methyl-4-thienyl)-1-methylethyl]amino]-1-oxobutyl]-N,N-dimethyl-4-piperidine carboxamide
18. 1-[4-[ethyl[2-(2-thienyl)-1-methylethyl]amino]-1-oxobutyl]-N,N-dimethyl-4-piperidine carboxamide
19. 1-[4-[ethyl[2-(4-methoxyphenyl)-1-methylethyl]amino]-1-oxobutyl]-N,N-dimethyl-4-piperidine thioamide
20. 1-[4-[ethyl[2-(4-methoxyphenyl)-1-methylethyl]amino]-1-oxo-2-butenyl]-N,N-dimethyl-4-piperidine carboxamide
21. 1-[4-[ethyl[2-(5-benzo[b]thienyl)-1-methylethyl]amino]-1-oxobutyl]-N,N-dimethyl-4-piperidine carboxamide
22. 1-[4-[ethyl[2-[5-(2,3-dihydro benzo[b]thienyl)]-1-methylethyl]amino]-1-oxobutyl]-N,N-dimethyl-4-piperidine carboxamide
23. 1-[4-[ethyl[2-(6-quinolyl)-1-methylethyl]amino]-1-oxobutyl]-N,N-dimethyl-4-piperidine carboxamide
24. 1-[4-[ethyl[2-[6-(1,2,3,4-tetrahydroquinolyl]-1-methylethyl]amino]-1-oxobutyl]-N,N-dimethyl-4-piperidine carboxamide
25. 1-[4-[ethyl[2-(4-dimethylaminophenyl)-1-methylethyl]amino]-1-oxobutyl]-N,N-dimethyl-4-piperidine carboxamide The following compounds were obtained by further conversion of the above compounds:
26. (S)-1-[4-[ethyl[2-(4-hydroxyphenyl)-1-methylethyl]amino]-1-oxobutyl]-N,N-dimethyl-4-piperidine carboxamide (starting from example I)
27. (S)-1-[4-[ethyl[2-(4-pivaloyloxyphenyl)-1-methylethyl]amino]-1-oxobutyl]-N,N-dimethyl-4-piperidine carboxamide (starting from 26)
28. (S)-1-[4-[ethyl[2-(4-benzoyloxyphenyl)-1-methylethyl]amino]-1-oxobutyl]-N,N-dimethyl-4-piperidine carboxamide (starting from 26)
29. 1-[4-[ethyl[2-(4-methoxyphenyl)-1-methylethyl]amino]-1-oxobutyl]4-piperidone (starting from 2.)
30. 1-[4-[ethyl[2-(4-methoxyphenyl)-1-methylethyl]amino]-1-oxobutyl]-4-hydroxy-4-methyl piperidine (starting from 29.)
31. 1-[4-[ethyl[2-(4-methoxyphenyl)-1-methylethyl]amino]-1 -oxobutyl]-4-piperidone oxim (starting from 29.)
32. 1-[4-[ethyl[2-(4-methoxyphenyl)-1-methylethyl]amino]-1-oxobutyl]-4-piperidone 0-methyloxim (starting from 29.)
33. (S)-1-[4-[ethyl[2-(4-methoxyphenyl)-1-methylethyl]amino]-1-oxobutyl]-4-formyl piperazine (starting from 3.)
34. (S)-1-[4-[ethyl[2-(4-methoxyphenyl)-1-methylethyl]amino]-1-oxobutyl]-4-acetyl piperazine (starting from 3.)
35. 1-[4-[ethyl[2-(4-methoxyphenyl)-1-methylethyl]amino]-1-oxobutyl]-4-benzoyl piperazine (starting from 4.)
36. 1-[4-[ethyl[2-(4-methoxyphenyl)-1-methylethyl]amino]-1-oxobutyl]-4-hydroxyacetyl piperazine (starting from 4.)
37. 1-[4-[ethyl[2-(4-methoxyphenyl)-1-methylethyl]amino]-1-oxobutyl]-4-carbethoxy piperazine (starting from 4.)

EXAMPLE II (S)-1-[4-[ethyl[2-(4-methoxyphenyl)-1-methylethyl]amino]-1-oxobutyl]-4-N,N-dimethylamino piperidine.

2.80 g (10 mmol) of (S)-4-[ethyl[2-(4-methoxyphenyl)-1-methylethyl]amino butanoic acid were dissolved in a mixture of 50 ml of dimethoxyethane and 10 ml of dichloroethane. This solution was added dropwise at 0°–5° C. to a solution of 1.01 g of triethyl amine (10 mmol) and 1.09 g of chloroformic acid ethyl ester (10 mmol) in 25 ml of dimethoxyethane. The reaction mixture was stirred at 0° C. for 2.5 hours, after which a solution of 1.28 g (10 mmol) of 4-dimethylamino piperidine in 50 ml of dimethoxyethane was added dropwise at 0°–5° C. The reaction mixture was stirred for one hour at room temperature, after which the solvent was evaporated under reduced pressure. The residue was dissolved in a mixture of water and methylene chloride. The organic layer was separated and the water layer was extracted another two times with methylene chloride. The combined organic layers were dried on sodium sulphate and evaporated under reduced pressure. The resulting crude reaction product was purified chromatographically over silicagel using a mixture of methylene chloride, methanol and concentrated ammonia in the ratio 90:9.5:0.5 as an eluent. The collected fractions contained 1.60 g (4.1 mmol) of (S)-1-[4-[ethyl[2-(4-methoxyphenyl)-1-methylethyl]amino]-1-oxobutyl]-4-N,N-dimethylamino piperidine. In an analogous manner were prepared:
38. 1-[4-[ethyl[2-(4-methoxyphenyl)-1-methylethyl]amino]-1-oxobutyl]piperidine
39. 1-[4-[ethyl[2-(4-methoxyphenyl)-1-methylethyl]amino]-1-oxobutyl]pyrrolidine
40. 1-[4-[ethyl[2-(3-fluoro-4-methoxyphenyl)-1-methylethyl]-amino]-1-oxobutyl]-4-N,N-dimethylamino piperidine'

41. 1-[2-methyl-4-[ethyl[2-(4-methoxyphenyl)-1-methylethyl]amino]-1-oxobutyl]-4-hydroxy piperidine 42. 1-[4-[ethyl[2-(4-methoxyphenyl)-1-methylethyl]amino]-1-oxo-3-methyl-2-butenyl]-N,N-dimethylamino-4-piperidine carboxamide.

EXAMPLE III (S)-4-[4-[ethyl[2-(4-methoxyphenyl)-1-methylethyl]amino]-1-oxobutyl]thiomorpholine.

25.28 g (80 mmol) of (S)-4-[4-[ethyl[2-(4-methoxyphenyl)-b 1-methylethyl]amino butanoic acid hydrochloride were suspended in 75 ml of thionylchloride and stirred under nitrogen at 55° C. for 2 hours.

The thionyl chloride was distilled off under reduced pressure and the resulting solid acid chloride was suspended in 100 ml of dry acetonitrile and added, while stirring, at 0°–5° C. to a solution of 25.0 g (240 mmol) of thiomorpholine in 200 ml of dry acetonitrile.

The reaction mixture was stirred for one hour at room temperature and the acetonitrile was then distiled off under reduced pressure. The residue was dissolved in a mixture of methylene chloride and water; the organic layer was separated and the water layer was extracted another two times with methylene chloride.

The combined organic layers were dried on sodium sulphate and evaporated under reduced pressure. The resulting crude reaction product was purified chromatographically over silicagel using a mixture of methylene chloride, methanol and concentrated ammonia in the ratio 90:9.5:0.5 as an eluent.

The collected fractions contained 10.4 g (28.5 mmol) of (S)-4-[4-[ethyl[2-(4-methoxyphenyl)-1-methylethyl]amino]-1-oxobutyl]thiomorpholine. In an analogous manner were prepared:

43. (S)-1-[4-[ethyl[2-(4-methoxyphenyl)-1-methylethyl]amino]-1-oxobutyl]-4-hydroxy piperidine
44. 1-[4-[ethyl[2-(4-methoxyphenyl)-1-methylethyl]amino]-1-oxobutyl]-4-hydroxy piperidine (racemate of 43.)
45. 1-[4-[ethyl[2-(4-methoxyphenyl)-1-methylethyl]amino]-1-oxobutyl]-4-hydroxy-4-(4-chlorophenyl) piperidine
46. 1-[4-[ethyl[2-(4-methoxyphenyl)-1-methylethyl]amino]-1-oxobutyl]-3-hydroxy piperidine
47. 1-[4-[ethyl[2-(4-methoxyphenyl)-1-methylethyl]amino]-1-oxobutyl]-2-methyl-4-hydroxy piperidine
48. 1-[4-[ethyl[2-(4-methoxyphenyl)-1-methylethyl]amino]-1-oxobutyl]-4-hydroxymethyl piperidine
49. 1-[4-[ethyl[2-(4-methoxyphenyl)-1-methylethyl]amino]-1-oxobutyl]-5-hydroxy perhydro azocine
50. 8-[4-[ethyl[2-(4-methoxyphenyl)-1-methylethyl]amino]-1-oxobutyl]-8-azabicyclo-[3.2.1]octan-3-one
51. 1-[4-[ethyl[2-(4-methoxyphenyl)-1-methylethyl]amino]-1-oxobutyl]-4-N-methylamino piperidine
52. 1-[4-[ethyl[2-(4-methoxyphenyl)-1-methylethyl]amino]-1-oxobutyl]-4-N-acetylamino piperidine
53. 1-[4-[ethyl[2-(4-methoxyphenyl)-1-methylethyl]amino]-1-oxobutyl]-4-carbethoxy piperidine
54. 1-[4-[ethyl[2-(4-methoxyphenyl)-1-methylethyl]amino]-1-oxobutyl]-N,N-dimethyl-4-piperidine sulfonamide
55. 1-[4-[ethyl[2-(4-methoxyphenyl)-1-methylethyl]amino]-1-oxobutyl]-4-(2-hydroxyethyl)piperazine
56. 1-[4-[ethyl[2-(4-methoxyphenyl)-1-methylethyl]amino]-1-oxobutyl]piperazin-3-one
57. 1-[3-[ethyl[2-(4-methoxyphenyl)-1-methylethyl]amino]propylsulphonyl]-4-hydroxy piperidine
58. 1-[5-[ethyl[2-(4-methoxyphenyl)-1-methylethyl]amino]-1-oxopentyl]-4-hydroxy piperidine
59. 1-[4-[ethyl[2-(4-methoxyphenyl)-1-methylethyl]amino]-1-oxobutyl]-4-hydroxy piperidine
60. 1-[4-[cyclopropyl[2-(4-methoxyphenyl)-1-methylethyl]amino]-1-oxobutyl]-4-hydroxy piperidine
61. 1-[4-[1-methylethyl[2-(4-methoxyphenyl)-1-methylethyl]amino]-1-oxobutyl]-4-hydroxy piperidine
62. 1-[4-[ethyl[2-(4-chlorophenyl)-1-methylethyl]amino]-1-oxobutyl]-4-hydroxy piperidine
63. 1-[4-[ethyl[2-[5-(2-methyl)-pyridyl]-1-methylethyl]amino]-1-oxobutyl]-4-hydroxy piperidine
64. 1-[4-[ethyl[2-[6-(2,3-dihydrobenzo[b]pyranyl)]-1-methylethyl]amino]-1-oxobutyl]-4-hydroxy piperidine
65. 1-[4-[ethyl[2-(3,4-methylenedioxyphenyl)-1-methylethyl]-amino]-1-oxobutyl]-4-hydroxy piperidine
66. 1-[4-[ethyl[2-(3,4-ethylenedioxyphenyl)-1-methylethyl]-amino]-1-oxobutyl]-4-hydroxy piperidine
67. 1-[4-[ethyl[2-(5-benzo[b]furyl)-1-methylethyl]amino]-1-oxobutyl]-N,N-dimethyl-4-piperidine carboxamide
68. 1-[4-[ethyl[2-[5-(2-methyl)-1,3-diazinyl]-1-methylethyl]amino]-1-oxobutyl]-N,N-dimethyl-4-piperidine carboxamide
69. 1-[4-methyl-4-[ethyl[2-(4-methoxyphenyl)-1-methylethyl]-amino]-1-oxobutyl]-4-hydroxy piperidine.

The following compounds were obtained by further conversion of the above mentioned compounds:

70. (S)-4-[4-[ethyl[2-(4-methoxyphenyl)-1-methylethyl]amino]-1-oxobutyl]thiomorpholine-1-oxide (starting from Example III)
71. (S)-4-[4-[ethyl[2-(4-methoxyphenyl)-1-methylethyl]amino]-1-oxobutyl]thiomorpholine-1,1-dioxide (starting from Example III)
72. 1-[4-[ethyl[2-(4-methoxyphenyl)-1-methylethyl]amino]-1-oxobutyl]-4-methoxy piperidine (starting from 44.)
73. 1-[4-[ethyl[2-(4-methoxyphenyl)-1-methylethyl]amino]-1-oxobutyl]-4-acetyloxy piperidine (starting from 44)
74. 1-[4-[ethyl[2-(4-methoxyphenyl)-1-methylethyl]amino]-1-oxobutyl]-4-pivaloyloxy piperidine (starting from 44)
75. 1-[4-[ethyl[2-(4-methoxyphenyl)-1-methylethyl]amino]-1-oxobutyl]-4-aspariginyloxy piperidine (starting from 44)
76. 1-[4-[ethyl[2-(4-methoxyphenyl)-1-methylethyl]amino]-1-oxobutyl]-4-glycyloxy piperidine (starting from 44)
77. 1-[4-[ethyl[2-(4-hydroxyphenyl)-1-methylethyl]amino]-1-oxobutyl]-4-hydroxy piperidine (starting from 44)
78. 1-[4-[ethyl[2-(3-hydroxymethyl-4-methoxyphenyl)-1-methylethyl]amino]-1-oxobutyl]-4-hydroxy piperidine (starting from 44)
79. 8-[4-[ethyl[2-(4-methoxyphenyl)-1-methylethyl]amino]-1-oxobutyl]-8-azabicyclo-[3.2.1]octan-3-ol (starting from 50)
80. 1-[4-[ethyl[2-(4-methoxyphenyl)-1-methylethyl]amino]1-oxobutyl]-4-[N-methyl-N-formylamino]-piperidine (starting from 51)

81. 1-[4-[ethyl[2-(4-methoxyphenyl)-1-methylethyl]amino]-1-oxobutyl]-4-piperidine carboxamide (starting from 53)
82. 1-[4-[ethyl[2-(4-methoxyphenyl)-1-methylethyl]amino]-1-oxobutyl]-N-methyl-4-piperidine carboxamide (starting from 53)
83. 1-[4-[ethyl[2-(4-methoxyphenyl)-1-methylethyl]amino]-1-oxobutyl]-N-ethyl-4-piperidine carboxamide (starting from 53)
84. 1-[4-[ethyl[2-(4-methoxyphenyl)-1-methylethyl]amino]-1-oxobutyl]-N-methoxy, N-methyl-4-piperidine carboxamide (starting from 53)
85. 1-[4-[ethyl[2-(4-methoxyphenyl)-1-methylethyl]amino]-1-oxobutyl]-N,N-diethyl-4-piperidine carboxamide (starting from 53)
86. 1-[4-[ethyl[2-(4-methoxyphenyl)-1-methylethyl]amino]-1-oxobutyl]-4-pipridine-[4-hydroxy-1-piperidino]carboxamide (starting from 53)
87. 1-[4-[ethyl[2-(4-methoxyphenyl)-1-methylethyl]amino]-1-oxobutyl]-4-acetyl piperidine (starting from 84).

EXAMPLE IV

1-[2-[ethyl[2-(4-methoxyphenyl)-1-methylethyl]amino]ethyl-N-methylcarbamoy]-N,N-dimethyl-4-piperidine carboxamide.

0.97 ml (7 mmol) of triethylamine were added to 1.75 g (7 mmol) of ethyl-[2-(N-methyl)ethyl]-[2-(4-methoxyphenyl)-1-methylethyl]amine dissolved in 50 ml of dry acetonitrile and 0.69 g (7 mmol) of phosgene gas was then led through. After stirring at room temperature for 2 hours 2.18 g (14 mmol) of N,N-dimethyl-4-piperidine carboxamide were added and the reaction mixture was refluxed for 2 hours. After evaporating the reaction mixture under reduced pressure, the residue was dissolved in a mixture of 50 ml of water and 100 ml of dichloromethane. The organic layer was washed once with water, dried on sodium sulphate and evaporated under reduced pressure. The crude reaction product was purified chromatographically over silicagel using a mixture of methylene chloride, methanol and concentrated ammonia in the ratio 90:9.5:0.5 as an eluent. The collected fractions contained 0.9 g (2 mmol) of 1-[2-[ethyl[2-(4-methoxyphenyl)-1-methylethyl]amino]-ethyl-N-methylcarbamoyl]-N,N-dimetyl-4-piperidine carboxamide. In an analogous manner were prepared:

88. 1-[2-[ethyl[2-(4-methoxyphenyl)-1-methylethyl]amino]ethyl-N-ethylcarbamoyl]-N,N-dimethyl-4-piperidine carboxamide
89. 1-[2-[ethyl[2-(4-methoxyphenyl)-1-methylethyl]amino]ethylcarbamoyl]-N,N-dimethyl-4-piperidine carboxamide
90. 1-[2-[ethyl[2-(4-methoxyphenyl)-1-methylethyl]amino]carbethoxy]-N,N-dimethyl-4-piperidine carboxamide
91. 1-[2-[ethyl[2-(4-methoxyphenyl)-1-methylethyl]amino]ethyl-N-methylsulfamoyl]-N,N-dimethyl-4-piperidine carboxamide

EXAMPLE V

1-[4-[ethyl[2-(4-methoxyphenyl)-1-methylethyl]amino]-1-thioxobutyl]piperidine.

2.02 g (5 mmol) of 2,4-bis(4-methoxyphenyl)-1,3,2,4-dithiadiphosphetane 2,4 disulphide were added to 3.46 g (10 mmol) of 1-[4-[ethyl[2-(4-methoxyphenyl)-1-methylethyl]amino]-1-oxobutyl]piperidine dissolved in 50 ml of dry tetrahydrofuran. The reaction mixture was stirred at room temperature for 18 hours and then evaporated under reduced pressure. The crude reaction product was purified chromatographically over silicagel using a mixture of methylene chloride, methanol and concentrated ammonia in the ratio 92'7.5'0.5 as an eluent. The collected fractions contained 0.80 g (2.2 mmol) of 1-[4-[ethyl[2-(4-methoxyphenyl)-1-methylethyl]amino]-1-thioxobutyl]piperidine. In an analogous manner was prepared 92. 1-[4-[ethyl[2-(4-methoxyphenyl)-1-methylethyl]amino]-1-thioxobutyl]-N,N-dimethyl-4-piperidine thioamide.

We claim:

1. A spasmolytically active tertiary amine derivative, acid addition salts and prodrugs thereof of the formula:

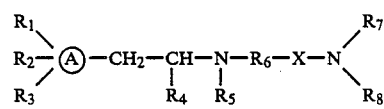

wherein
Ⓐ is a phenyl nucleus;
$R_1$ and $R_2$ may be equal or different and are hydrogen, alkyl having 1–3 carbon atoms, hydroxylalkyl or mercaptoalkyl having 1–3 carbon atoms which may be etherified or esterified, alkoxy having 1–3 carbon atoms, the group $S(O)_m$—$R_9$, wherein $R_9$ is an alkyl group having 1–3 carbon atoms, and m has the value 0, 1 or 2, a group - $NR_{10}R_{11}$, wherein $R_{10}$ and $R_{11}$ represent alkyl having 1–3 carbon atoms, or together may form a saturated, 5 or 6 membered ring optionally containing a member selected from the group consisting of sulphur, oxygen and nitrogen; hydroxy group, mercapto group or amino group, which groups may be derived with an easily removable ester group or ether group; or a halogen atom, or $R_1$ and $R_2$ together may form a 5- or 6- membered saturated ring optionally containing 1 or 2 members selected from the group consisting of oxygen, nitrogen and sulphur atoms, which ring is condensed with the phenyl nucleus and may by substituted with one or more alkyl groups having 1–3 carbon atoms, optionally etherified or esterified hydroxyalkyl having 1–3 carbon atoms or with an oxygen atom;
$R_1$ is a hydrogen atom or, together with $R_4$, may form a ring consisting of 6 or 7 carbon atoms;
at least one of $R_1$, $R_2$ and $R_3$ being other than hydrogen;
$R_4$ is a hydrogen atom or alkyl group having 1–3 carbon atoms;
$R_5$ is a straight, branched or cyclic alkyl group having 1–4 carbon atoms;
$R_6$ is a straight or branched, saturated or unsaturated alkylene group having a chain length of 3–6 carbon atoms;
X is a carbonyl group, thiocarbonyl group or $SO_2$ group;
$R_7$ and $R_8$, together with the nitrogen atom to which they are bound, constitute a fully or partly saturated heterocyclic ring consisting of 5–8 ring atoms optionally containing an oxygen, nitrogen or sulfur atom as the second hetero atom, and optionally containing at least one member selected from the group [consisting of members selected from the group] consisting of 1 to 2 alkyl groups having 1–3 carbon atoms, an alkylene bridge of 2 or 3 carbon atoms across the ring; or oxygen, provided that when the substituent is oxygen having a keto function it has the form of a ketal or oxim, or the ring formed by the $R_7$ and $R_8$ may be substituted directly or via an alkylene chain of 1-3 carbon atoms, with 1 or 2 members selected from the group consisting of phenyl, optionally containing halogen; alkyl or alkoxy having 1-3 carbon atoms, hydroxy, amino, mono- or dialkylamino having 1-3 carbon atoms in the alkyl group(s), alkanoyl or thioalkanoyl having 1-3 carbon atoms, hydroxy alkanoyl having 1-3 carbon atoms, benzoyl, optionally esterified or etherified hydroxy or mercapto, optionally mono- or dialkyl or -acyl substituted amino, carbalkoxy having 1-3 carbon atoms in the alkoxy group, a carbamoyl, thio carbamoyl, sulfamoyl or carbamoyloxy group of which the nitrogen atom may be substituted by 1 or 2 alkoxy groups having 1-3 carbon atoms or alkyl groups having 1-5 carbon atoms, which, via a nitrogen, oxygen or sulphur atom, may form a saturated heterocyclic group consisting of 5 or 6 ring atoms.

2. Compounds as claimed in claim 1 of the formula (1) wherein Ⓐ is the phenyl group, $R_1$ is the p-methoxy group, $R_2$ and $R_3$ are hydrogen, $R_4$ is the methyl group, $R_5$ is the ethyl group, and X is the carbonyl group, the group $-NR_7R_8$ has one of the following meanings:

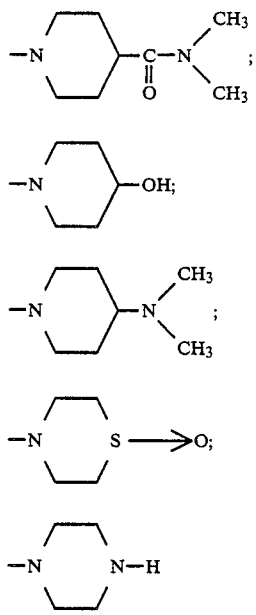

and the carbon atoms to which $R_4$ is bound and acid addition salts and prodrugs thereof.

3. Spasmolytically active compositions, characterized in that they comprise at least one compound of claim 1 as the active component in form suitable for administration.

* * * * *